(12) United States Patent
Hirose

(10) Patent No.: US 8,068,656 B2
(45) Date of Patent: Nov. 29, 2011

(54) X-RAY INSPECTION APPARATUS

(75) Inventor: Osamu Hirose, Shiga (JP)

(73) Assignee: Ishida Co., Ltd., Kyoto (JP)

( * ) Notice: Subject to any disclaimer, the term of this patent is extended or adjusted under 35 U.S.C. 154(b) by 905 days.

(21) Appl. No.: 12/089,473

(22) PCT Filed: Nov. 15, 2006

(86) PCT No.: PCT/JP2006/322762
§ 371 (c)(1),
(2), (4) Date: Apr. 7, 2008

(87) PCT Pub. No.: WO2007/058212
PCT Pub. Date: May 24, 2007

(65) Prior Publication Data
US 2009/0147987 A1    Jun. 11, 2009

(30) Foreign Application Priority Data
Nov. 16, 2005    (JP) .................................. 2005-331540

(51) Int. Cl.
*A61B 6/03*    (2006.01)
(52) U.S. Cl. ............ 382/132; 378/54; 378/57; 378/207; 701/101
(58) Field of Classification Search .......... 382/131–132; 378/54, 57, 205, 207; 701/101
See application file for complete search history.

(56) References Cited

U.S. PATENT DOCUMENTS

| | | |
|---|---|---|
| 4,692,616 A | 9/1987 | Hegland et al. |
| 4,990,784 A | 2/1991 | Dukes et al. |
| 5,585,603 A * | 12/1996 | Vogeley, Jr. ................. 177/25.13 |
| 6,201,850 B1 * | 3/2001 | Heumann ......................... 378/56 |
| 6,347,131 B1 * | 2/2002 | Gusterson ....................... 378/54 |
| 6,385,284 B1 | 5/2002 | Parmee |
| 2005/0023464 A1 | 2/2005 | Sturm |
| 2010/0256952 A1 * | 10/2010 | Dekker ........................ 702/180 |

FOREIGN PATENT DOCUMENTS

| | | |
|---|---|---|
| JP | S60-014128 A | 1/1985 |
| JP | 2002-520593 A | 7/2002 |
| JP | 2002-296022 A | 10/2002 |

OTHER PUBLICATIONS

Extended European Search Report dated Jan. 10, 2011 for the counterpart European Patent Application No. 06823410.3.

* cited by examiner

Primary Examiner — Edward Glick
Assistant Examiner — John Corbett
(74) Attorney, Agent, or Firm — Global IP Counselors, LLP

(57) ABSTRACT

An x-ray inspection apparatus includes a sample image obtaining unit, an ideal curve generating unit, a curve adjustment unit, and a mass estimation unit as a function block generated by a control computer. The sample image obtaining unit obtains 10 x-ray transmission images of sample inspected products each of whose mass is known in advance. The ideal curve generating unit generates a table based on a formula that indicates a relationship between the brightness of an area included in the x-ray transmission images and the estimated mass of the area. The curve adjustment unit refers to the input actual mass of each x-ray transmission image and adjusts the table such that the estimated mass approximates the actual mass. The mass estimation unit determines the estimated mass per unit area based on the post-adjusted table and adds up these masses to determine the total estimated mass of the product.

12 Claims, 16 Drawing Sheets

| OPTIMIZATION OF CONVERSION TABLE | EVEN | UNEVEN | DIFFERENCE |
|---|---|---|---|
| BEFORE | 10.34 (g) | 9.79 (g) | 0.55 (g) |
| AFTER | 10.03 (g) | 9.95 (g) | 0.08 (g) |

Fig. 13

X-RAY INSPECTION APPARATUS

CROSS-REFERENCE TO RELATED APPLICATIONS

This application is a U.S. National Phase application of the international application No. PCT/JP2006/322762 filed on Nov. 15, 2006, which claims priority to Japanese Patent Application No. 2005-331540 filed on Nov. 16, 2005. The entire disclosure of Japanese Patent Application No. 2005-331540 is hereby incorporated herein by reference.

TECHNICAL FIELD

The present invention relates to an x-ray inspection apparatus configured to estimate the mass of material based on an x-ray transmission image obtained by irradiating x-rays to the material.

BACKGROUND DART

In recent years, an x-ray mass estimation apparatus is used in which x-rays are irradiated to a measurement target object and the mass of the measurement target object is estimated (calculated) based on the amount of x-rays transmitted through the measurement target object.

With this x-ray mass estimation apparatus, an x-ray transmission image of the measurement target object is obtained, and then, by utilizing a characteristic that the image appears darker when the thickness of material in the x-ray transmission image is larger, the mass of the measurement target object is estimated according to the brightness per unit area included in the x-ray transmission image, for example, when the brightness is low, the mass is large, and when the brightness is high, the mass is small.

Specifically, given that the image brightness when there is no material is $I_0$, the image brightness of a portion where x-rays are transmitted through material is I, and the thickness of material is t, a relationship among these factors is expressed by the following relational expression (1).

$$I/I_0 = e^{-\mu t} \tag{1}$$

Here, the value $\mu$ denotes a linear mass coefficient determined by x-ray energy and the type of material, indicating that the higher the value is, the greater the amount of x-rays that is absorbed.

Also, in order to estimate the thickness of the material from the brightness of the image, the following relational expression (2) is used.

$$t = -1/\mu \times \ln(I/I_0) \tag{2}$$

In order to convert these values to the mass m, the following relational expression (3) is used in which an adequate coefficient is used as a multiplication factor.

$$m = ct = -c/\mu \times \ln(I/I_0) = -\alpha \ln(I/I_0) \tag{3}$$

(Note that the value "c" denotes a coefficient for converting the thickness of the material to the mass m)

Typically, an x-ray transmission image is formed by a plurality of pixels, thus it is possible to estimate the mass of the entire material by determining the mass m for each pixel and adding up these masses for the entire image. This can be expressed by the following formula (4).

$$M = \Sigma\Sigma m(x,y) \tag{4}$$

For example, in the Japanese Laid-Open Patent Application Publication No. 2002-296022 (published on Oct. 9, 2002), an x-ray mass estimation apparatus is disclosed, in which x-rays are irradiated to the measurement target object; x-rays transmitted therethrough are detected; the mass of the measurement target object is calculated per unit transmission area based on the amount of transmitted x-rays from a predetermined formula; and the calculated unit mass of the measurement target object per unit transmission area is integrated over the entire x-ray transmission area.

DISCLOSURE OF THE INVENTION

However, the conventional x-ray mass estimation apparatus described above has the following problems.

In other words, with the x-ray mass estimation apparatus disclosed in the above publication, the mass of the material is calculated per unit transmission area from the predetermined formula and then the unit mass is integrated over the entire area in order to determine the entire mass. However, the x-ray photon energy is not monoenergetic but it forms a continuous spectrum, thus it is not possible to estimate the mass with high accuracy by means of the mass estimation method based on the formula.

Further, the brightness of an x-ray transmission image changes by the influence of uncertain factors such as specific filter, energy characteristics of the x-ray inspection apparatus, factors relating to image preprocessing such as gamma correction, and the like in addition to the thickness of materials. Accordingly, there are cases where the mass of an inspected object cannot be accurately estimated.

Therefore, it is an object of the present invention to provide an x-ray inspection apparatus capable of estimating the mass of material with high accuracy by eliminating the influence of various uncertain factors such as x-ray energy characteristics and specific filter.

An x-ray inspection apparatus according to a first aspect of the present invention is an x-ray inspection apparatus adapted to estimate a mass of an inspected object based on an amount of transmitted x-rays that are irradiated to the inspected object, the x-ray inspection apparatus comprising: an irradiation unit, an x-ray detection unit, a sample image obtaining unit, an input unit, an ideal curve generating unit, a curve adjustment unit, and a mass estimation unit. The irradiation unit is configured and arranged to irradiate x-rays to the inspected object. The x-ray detection unit is configured to detect the amount of x-rays that are irradiated by the irradiation unit and transmitted through the inspected object. The sample image obtaining unit is configured to obtain x-ray transmission images of a plurality of the inspected objects, based on the amount of x-rays irradiated to the plurality of inspected objects and detected by the x-ray detection unit. The input unit is configured to which actual masses of the inspected objects whose x-ray transmission images are obtained are input. The ideal curve generating unit is configured to generate an ideal curve which indicates a relationship between the brightness per unit area included in the x-ray transmission images and the corresponding mass per unit area. The curve adjustment unit is configured to adjust the ideal curve generated by the ideal curve generating unit for each gradation level based on the actual masses input in the input unit. The mass estimation unit is configured to estimate the mass of the inspected object based on the ideal curve adjusted for each gradation level by the curve adjustment unit.

Here, x-rays are irradiated to a plurality of inspected objects of which actual masses are known in advance and a sample image (x-ray transmission image) of each inspected object is obtained. Then, an ideal curve that indicates a relationship between the mass per unit area in the sample image and the brightness per unit area is generated. Then, the mass of the inspected object which is estimated based on this ideal curve is compared to the actual mass of the inspected object, and the ideal curve is adjusted such that the estimated mass of the inspected object approximates the actual mass. In accordance with the post-adjusted curve, the mass of the inspected object is estimated based on the brightness per unit area included in the x-ray transmission image obtained through actual inspection.

Here, the ideal curve is a curve represented by a graph or a table, which indicates a relationship between the brightness per unit area and the corresponding mass, and is represented by a formula.

Generally, with the method in which an ideal curve represented by a formula which indicates a relationship between the brightness and mass per unit area is obtained in order to determine the estimated mass as described above, there are cases where an error is generated between the actual mass and the ideal curve due to various uncertain factors which are not included in the formula, such as specific filter, energy characteristics of the x-ray inspection apparatus, factors relating to image preprocessing such as gamma correction, and the like. Therefore, with the mass estimation method which depends on the ideal curve represented by the formula, it is difficult to accurately estimate the mass.

With the x-ray inspection apparatus of the present invention, for estimation of the mass of the inspected object as described above, after an ideal curve is generated, the ideal curve is adjusted, for example, for each gradation level, such that the estimated mass calculated based on this ideal curve approximates the actual mass.

Accordingly, by adequately adjusting the ideal curve obtained based on a plurality of sample images in accordance with the actual mass, it is possible to obtain an ideal curve that accurately represents the brightness and mass per unit area. As a result, by obtaining an x-ray transmission image of the actual inspected object, adding up the mass per unit area calculated based on the post-adjusted ideal curve and estimating the mass of the inspected object, it is possible to estimate the mass with higher accuracy compared to the conventional apparatus.

An x-ray inspection apparatus according to a second aspect of the present invention is the x-ray inspection apparatus according to the first aspect of the present invention, wherein, the curve adjustment unit is configured to determine an estimated mass m+(a) and an estimated mass m−(a) within ±x % of an estimated mass m(a) that corresponds to a brightness "a" per unit area, to select one with a least variation among these estimated masses, and to adjust the ideal curve by replacing the estimated mass m(a) with the selected estimated mass.

Here, for the estimated mass per unit area, which is denoted by m(a), included in the x-ray transmission image of the inspected object, the estimated mass m−(a) and the estimated mass m+(a) within ±x % of the estimated mass m(a) are determined, a table (graph) with a least variation among them is selected, the estimated mass (a) is replaced with the value of the table (graph), and thereby the ideal curve is adjusted.

Accordingly, by gradually shifting the estimated mass m(a) and selecting a table (graph) with the least variation, it is possible to adequately correct the ideal curve and determine the estimated mass with high accuracy.

An x-ray inspection apparatus according to a third aspect of the present invention is the x-ray inspection apparatus according to the second aspect of the present invention, wherein the curve adjustment unit is configured to repeat replacing the estimated mass m(a) until the brightness "a" reaches a predetermined gradation level.

Here, for example, replacement of the above mentioned estimated mass m(a) is repeated by increasing the brightness "a" by 10 levels of gradation from the minimum gradation level 10 to the maximum gradation level 210.

Accordingly, it is possible to adjust the ideal curve in each gradation level such that the ideal curve uniformly approximates the actual mass. As a result, since the ideal curve can be adequately adjusted in accordance with each gradation level, it is possible to obtain the estimated mass with higher accuracy.

An x-ray inspection apparatus according to a fourth aspect of the present invention is the x-ray inspection apparatus according to the second aspect or the third aspect of the present invention, wherein the curve adjustment unit is configured to repeat replacing the estimated mass m(a) until the variation in the estimated mass m(a) falls within a predetermined range.

Here, the curve adjustment unit repeats adjusting the ideal curve until the variation in the estimated mass m(a) becomes within a predetermined range.

Accordingly, since adjustment of the curve is repeated until the estimated mass m(a) approximates the actual mass without variation, it is possible to more adequately adjust the ideal curve. As a result, it is possible to obtain a post-adjusted ideal curve with higher accuracy and obtain the estimated mass with high accuracy which is approximate to the actual mass.

In addition, when combining the condition in which the process is repeated until this variation becomes within a predetermined range and the condition in which the process is repeated until a predetermined gradation level is obtained, it is possible to adjust the ideal curve over the entire gradation levels such that the curve is adequately adjusted and such that the curve has less variation. As a result, it is possible to obtain a post-adjusted ideal curve with higher accuracy and obtain the estimated mass with high accuracy, which is approximate to the actual mass.

An x-ray inspection apparatus according to a fifth aspect of the present invention is the x-ray inspection apparatus according to any one of the second aspect to the fourth aspect of the present invention, wherein the curve adjustment unit is configured to repeat replacing the estimated mass m(a) for a predetermined number of times.

Here, the curve adjustment unit repeats adjusting the ideal curve for a predetermined number of times.

Accordingly, since the replacement process is terminated when replacement for a predetermined number of times is completed, it is possible to efficiently adjust the ideal curve. As a result, it is possible to efficiently obtain a post-adjusted ideal curve with high accuracy and obtain the estimated mass with high accuracy, which is approximate to the actual mass. In addition, when all of the above described termination conditions are combined, it is possible to obtain an adjusted ideal curve with high accuracy and accurately estimate the mass.

An x-ray inspection apparatus according to a sixth aspect of the present invention is the x-ray inspection apparatus according to any one of the second aspect to the fifth aspect of the present invention, wherein the curve adjustment unit is configured to repeat replacing the estimated mass m(a) until a predetermined period of time elapses.

Here, the curve adjustment unit repeats adjusting the ideal curve until a predetermined period of time elapses.

Accordingly, since the replacement is terminated when a predetermined period of time has elapsed, it is possible to prevent the replacement process of the estimated mass m(a) from taking a long time. As a result, it is possible to efficiently obtain a post-adjusted ideal curve with high accuracy and obtain the estimated mass with high accuracy, which is approximate to the actual mass. In addition, when all of the above described termination conditions are combined, it is possible to obtain an adjusted ideal curve with high accuracy and accurately estimate the mass.

An x-ray inspection apparatus according to a seventh aspect of the present invention is the x-ray inspection apparatus according to any one of the first aspect to the sixth aspect of the present invention, wherein the ideal curve generating unit is configured to calculate estimated masses m(a) by changing the brightness "a" for every ten levels of gradation and generates the ideal curve by linear interpolation of intermediate values.

Here, an ideal curve is generated by linear interpolation of intermediate values of the estimated masses m(a) obtained by substituting the brightness "a" to a formula for generating an ideal curve for every ten levels of gradation.

Accordingly, since the ideal curve can be efficiently generated, it is possible to efficiently obtain the estimated mass with high accuracy.

An x-ray inspection apparatus according to an eighth aspect of the present invention is the x-ray inspection apparatus according to any one of the first aspect to the seventh aspect of the present invention, wherein the ideal curve generating unit is configured to generate a table that indicates a relationship between the brightness "a" and the estimated mass m(a) based on a predetermined formula that represents a relationship between the brightness "a" per unit area in an x-ray transmission image and the corresponding estimated mass m(a).

Here, a table is generated based on a predetermined formula that indicates a relationship between the brightness "a" per unit area in an x-ray transmission image and the corresponding estimated mass m(a) of the area, and this table is adjusted such that the estimated mass m(a) approximates the actual mass based on the inputted actual mass.

Accordingly, by interpolation of intermediate values included in the table based on the table, it is possible to generate and adjust an ideal curve. As a result, it is possible to significantly reduce the time to calculate the estimated mass m(a), compared to the case where the brightness "a" is substituted into the formula to calculate the estimated mass m(a).

An x-ray inspection apparatus according to a ninth aspect of the present invention is the x-ray inspection apparatus according to any one of the first aspect to the eighth aspect of the present invention, wherein the unit area is equivalent to one pixel included in the x-ray transmission image.

Here, the mass corresponding to the brightness (gradation level) of each pixel unit included in the x-ray transmission image is estimated.

Accordingly, by determining the estimated mass for each pixel which is the minimum unit of the x-ray transmission image and by adding up these masses, it is possible to highly accurately calculate the estimated mass of the inspected object.

An x-ray inspection program according to a tenth aspect of the present invention is an x-ray inspection program configured to estimate a mass of an inspected object based on an amount of transmitted x-rays that are irradiated to the inspected object, wherein the x-ray inspection program causes a computer to run an x-ray inspection method comprising first through fifth steps. In the first step, the amount of x-rays that are irradiated to a plurality of inspected objects is detected, and x-ray transmission images of the plurality of inspected objects are obtained based on the amount of x-rays detected. In the second step, the actual masses of the inspected objects whose x-ray transmission images are obtained in the first step are input. In the third step, an ideal curve derived based on the brightness per unit area included in the x-ray transmission images and the corresponding mass per unit area is generated. In the fourth step, the ideal curve generated in the third step is adjusted for each gradation level based on the actual masses input in the second step. In the fifth step, the mass of the inspected object is estimated based on the ideal curve adjusted for each gradation level in the fourth step.

Here, x-rays are irradiated to the plurality of inspected objects whose actual masses are determined, and a sample image (x-ray transmission image) of each inspected object is obtained, and then the ideal curve that indicates a relationship between the mass per unit area included in the sample image and the corresponding brightness per unit area is generated. Then, the mass of the inspected object which is estimated based on this ideal curve is compared to the actual mass of the inspected object, and the ideal curve is adjusted such that the estimated mass of the inspected object approximates the actual mass. In accordance with the post-adjusted curve, the mass of the inspected object is estimated based on the brightness per unit area included in the x-ray transmission image obtained through actual inspection.

Here, the ideal curve is what is represented by a graph or a table which indicates a relationship between the brightness per unit area and the corresponding mass, and is represented by a formula.

Generally, with the method in which the ideal curve indicating a relationship between the brightness and mass per unit area, which is represented by a formula in this way is determined to estimate the mass, there are cases where an error is generated between the actual mass and the ideal curve due to various uncertain factors which are not included in the formula, such as specific filter, energy characteristics of the x-ray inspection apparatus, factors relating to image preprocessing such as gamma correction, and the like. Consequently, it was difficult to accurately estimate the mass by means of the mass estimation method that depends on the ideal curve represented by this formula.

With the x-ray inspection apparatus of the present invention, for estimation of the mass of the inspected object as described above, after an ideal curve is generated, the ideal curve is adjusted, for example, for each gradation, such that the estimated mass calculated based on this ideal curve approximates the actual mass.

Accordingly, by adequately adjusting the ideal curve obtained based on a plurality of sample images in accordance with their actual masses, it is possible to obtain an ideal curve that accurately represents the brightness and mass per unit area. As a result, by obtaining an x-ray transmission image of the actual inspected object, adding up the mass per unit area calculated based on the post-adjusted ideal curve, and estimating the mass of the inspected object, it is possible to estimate the mass at a higher accuracy than before.

An x-ray inspection apparatus according to an eleventh aspect of the present invention is the x-ray inspection apparatus according to any one of the first aspect to the sixth aspect of the present invention, wherein the ideal curve generating unit is configured to calculate estimated masses m(a) by changing the brightness "a" for every ten levels of gradation, and to generate an ideal curve by calculating a moving average of the function values obtained by linear interpolation of intermediate values.

Since this makes the ideal curve a smooth curve, it is possible to more highly accurately calculate the estimated mass by reducing variation (discontinuous changes) in the estimated mass values m(a), compared to a case where a graph generated by linear interpolation simply connecting calculated estimated mass values m(a).

An x-ray inspection apparatus according to a twelfth aspect of the present invention is the x-ray inspection apparatus according to any one of the first aspect to the sixth aspect of the present invention, wherein the ideal curve generating unit is configured to calculate estimated masses m(a) by changing the brightness "a" for every ten levels of gradation and to generate the ideal curve by linear interpolation of intermediate values.

Here, it is possible to perform the above mentioned curve interpolation by, for example, interpolation methods using Bezier curve (a method to approximate with N function), spline curve, and the like.

Since this makes the ideal curve a smooth curve, it is possible to more highly accurately calculate the estimated mass by reducing variation (discontinuous changes) in the estimated mass value m(a), compared to a case where a graph generated by linear interpolation simply connecting calculated estimated mass values m(a).

BRIEF DESCRIPTION OF THE DRAWINGS

FIG. 13 shows comparative results of the estimated masses of the products shown in FIG. 12A and FIG. 12B, which are obtained by using the conversion table m(a) optimized by the x-ray inspection apparatus of the present invention and the conversion table before optimization.

DETAILED DESCRIPTION OF PREFERRED EMBODIMENTS

An x-ray inspection apparatus according to a preferred embodiment of the present invention is described below with reference to FIGS. 1 through 13.

Overall Structure of an X-Ray Inspection Apparatus 10

Figure 1:
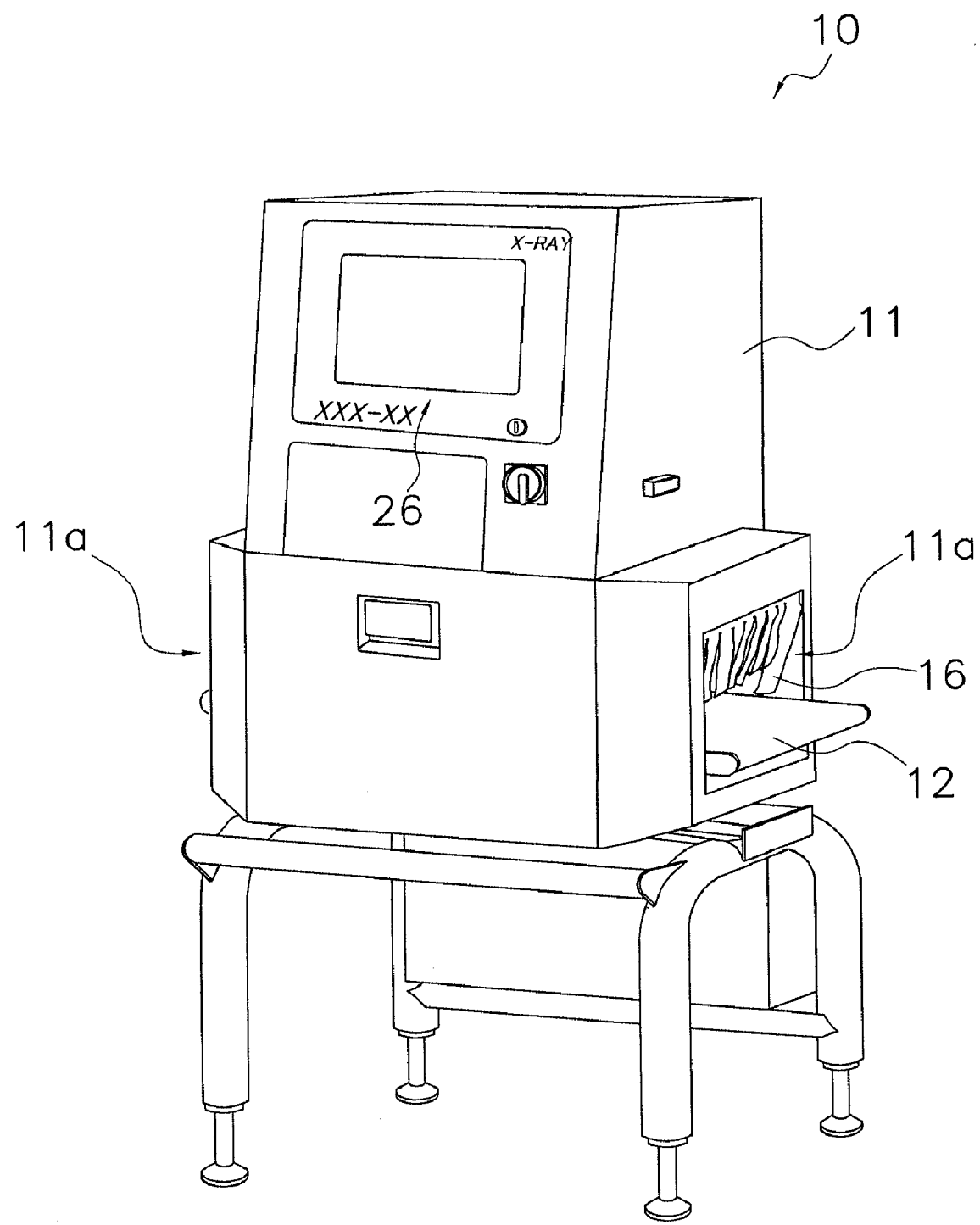
FIG. 1 is a perspective view of the external appearance of an x-ray inspection apparatus according to an embodiment of the present invention.

As shown in FIG. 1, the x-ray inspection apparatus 10 according to the embodiment of the present invention is an apparatuses that estimates the mass of food product such as a packaged powder soup product in production lines for food and other products. This x-ray inspection apparatus 10 irradiates x-rays to products that are transported thereto in a continuous manner, estimates the mass of the products based on x-ray images generated by detecting the amount of x-rays that are transmitted through the products, and determines whether or not the estimated mass is within a predetermined range.

Figure 2:
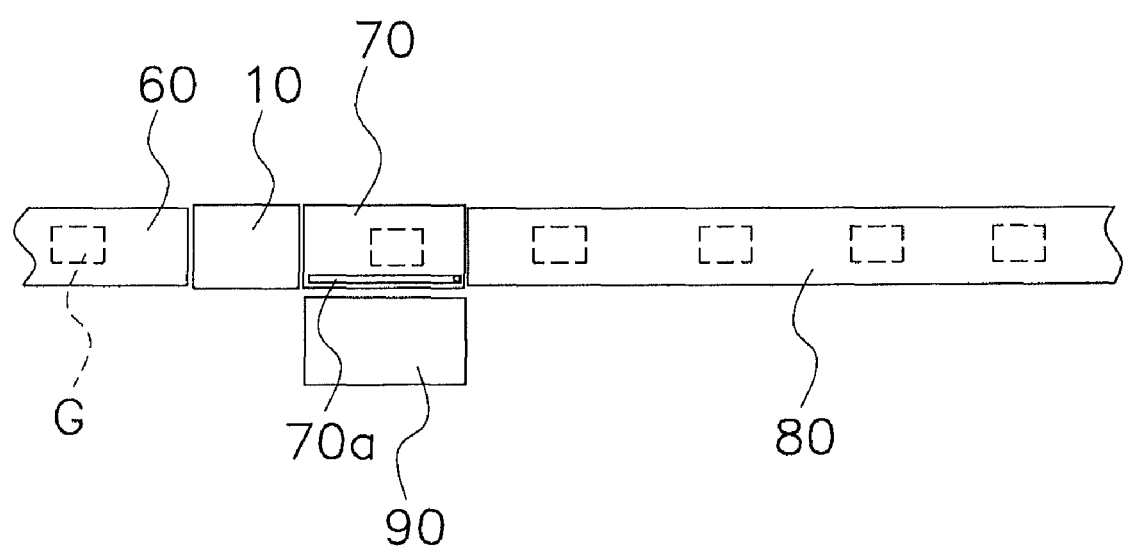
FIG. 2 is a view showing the structures in front of and behind the x-ray inspection apparatus of FIG. 1.

As shown in FIG. 2, a product G (inspected object) to be inspected by the x-ray inspection apparatus 10 is conveyed by a preceding conveyor 60 to the x-ray inspection apparatus 10. The mass of the product G is estimated based on an x-ray transmission image obtained by the x-ray inspection apparatus 10. The mass estimation results obtained by the x-ray inspection apparatus 10 are sent to a sorting mechanism 70 disposed downstream of the x-ray inspection apparatus 10. When the product G is determined as being within a predetermined mass range by the x-ray inspection apparatus 10, the sorting mechanism 70 sends the product G as is to a regular line conveyor 80. On the other hand, when the product G is determined as being outside of a predetermined mass range by the x-ray inspection apparatus 10, an arm 70a, which rotates around an end part on the downstream side, rotates so as to block a conveying path. In this way, it is possible to recall the product G which is determined as being outside of a predetermined mass range in a recall box 90 which is disposed at a position away from the conveying path.

Figure 3:
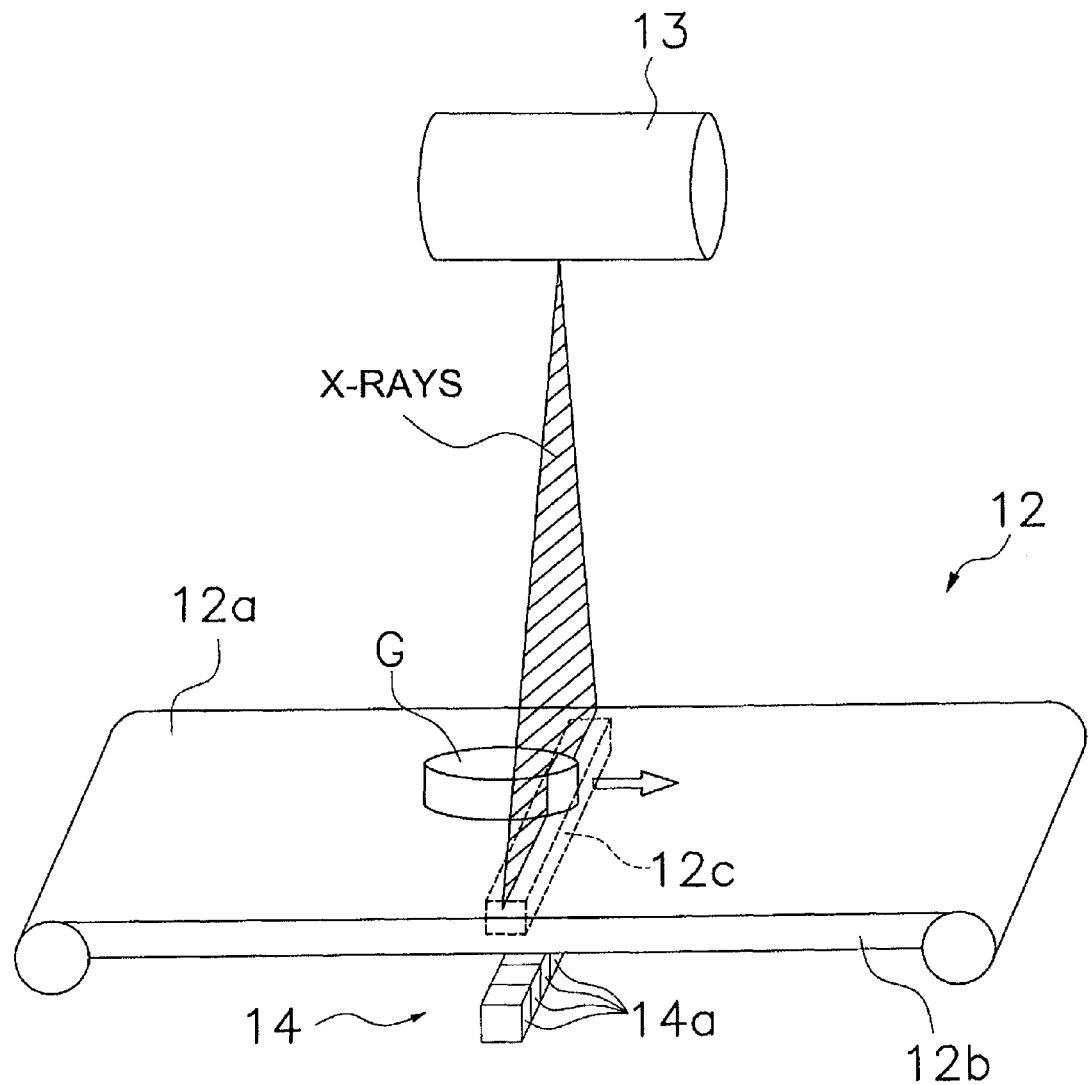
FIG. 3 is a simple schematic view of the inside of a shield box of the x-ray inspection apparatus of FIG. 1.

As shown n FIG. 1, the x-ray inspection apparatus 10 mainly comprises a shield box 11, a conveyor 12, a shielding curtain 16, and a monitor (input unit) 26 with a touch panel function. Further, as shown in FIG. 3, the inside of the x-ray inspection apparatus 10 is provided with an x-ray irradiator (irradiation unit) 13, an x-ray line sensor (x-ray detection unit) 14, and a control computer (sample image obtaining unit, ideal curve generating unit, curve adjustment unit, and mass estimation unit) 20 (see FIG. 5).

Shield Box 11

The shield box 11 has an opening 11a on an entrance side and an exit side for the product G, and through which products are transported into and out of the shield box 11. Inside this shield box 11 are housed the conveyor 12, the x-ray irradiator 13, the x-ray line sensor 14, the control computer 20 and the like.

As shown in FIG. 1, the opening 11a is covered with the shielding curtain 16 in order to prevent x-rays from leaking out of the shield box 11. The shielding curtain 16 is partially made of rubber that contains lead, and is pushed aside by a product when the product is carried in and out of the shield box 11.

In addition, on the upper part of the front surface of the shield box 11 are disposed a key hole and a power switch adjacent to the monitor 26.

Conveyor 12

Figure 5:
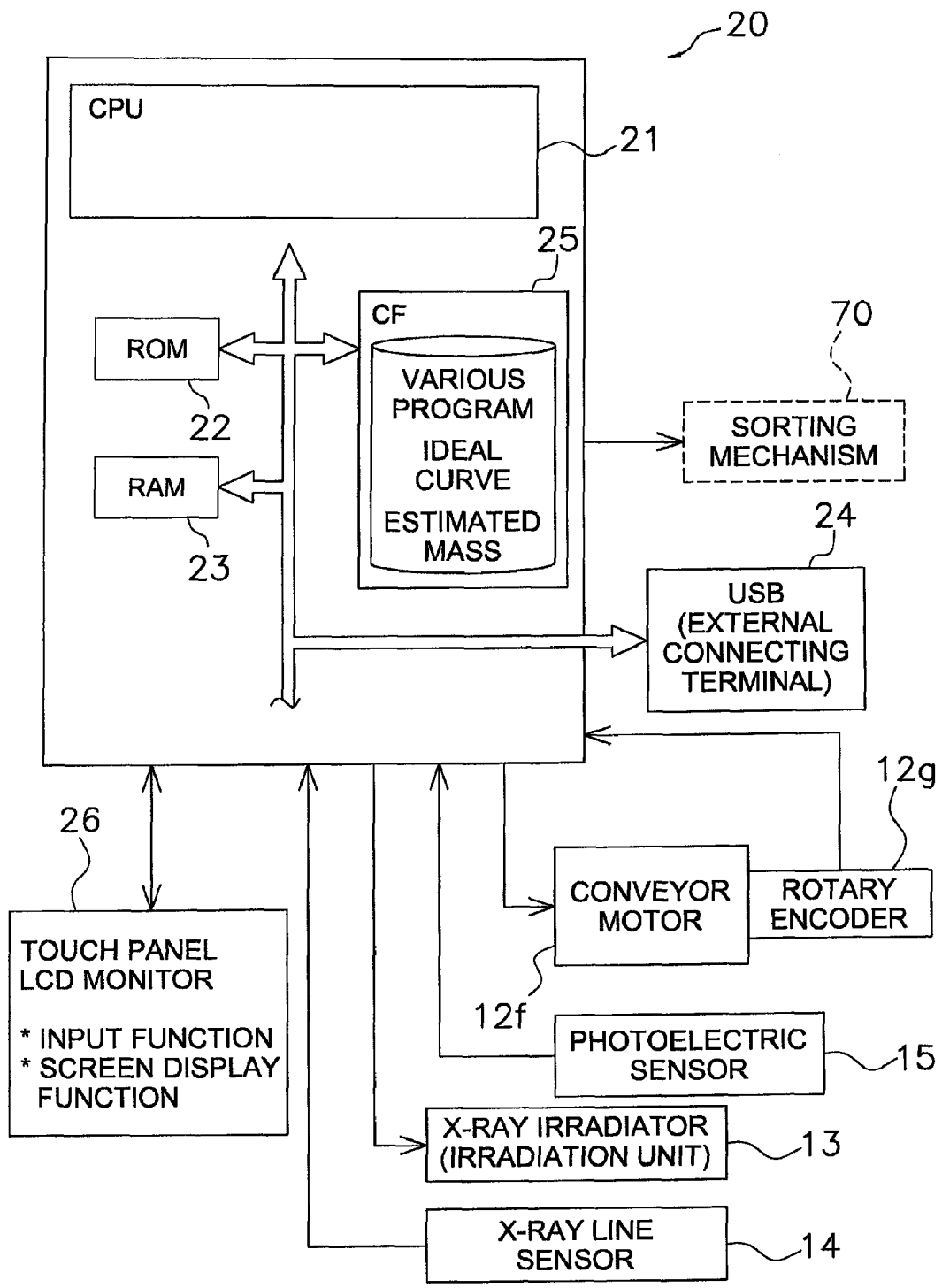
FIG. 5 is a control block diagram showing the structure of a control computer included in the x-ray inspection apparatus in FIG. 1.

The conveyor 12 serves to transport products into and out of the shield box 11, and is driven by a conveyor motor 12f included in the control block shown in FIG. 5. The transport speed of the conveyor 12 is precisely controlled through an inverter-control of the conveyor motor 12f by the control computer 20, so as to match the transport speed with the setting speed input by an operator.

In addition, as show in FIG. 3, the conveyor 12 includes a conveyor belt 12a and a conveyor frame 12b, which are removably attached to the shield box 11. In this way, when conducting inspection of a food product and the like, the conveyor 12 can be removed and washed frequently to keep the inside of the shield box 11 clean.

The conveyor belt 12a is an endless belt, and the inside of the belt is supported by the conveyor frame 12b. The conveyor belt 12a rotates by receiving a driving force of the conveyor motor 12f, and consequently the conveyor belt 12a conveys an object placed on the belt in a predetermined direction.

The conveyor frame 12b supports the endless the conveyor belt 12a from the inside thereof. Also, as shown in FIG. 3, the conveyor frame 12b has an opening 12c, which opens lengthwise in a direction perpendicular to the conveyance direction, at a position opposing the inner side of the conveyor belt 12a. The opening 12c is formed on a line, which connects the x-ray irradiator 13 and the x-ray line sensor 14, on the conveyor frame 12b. In other words, the opening 12c is formed at an area where x-rays are irradiated toward by the x-ray irradiator 13 on the conveyor frame 12b, in order to prevent the x-rays transmitted through the product G from being blocked by the conveyor frame 12b.

X-Ray Irradiator 13

As shown in FIG. 3, the x-ray irradiator 13 is disposed above the conveyor 12 and irradiates fan-shaped x-rays through the opening 12c formed in the conveyor frame 12b toward the x-ray line sensor 14 disposed below the conveyor 12 (see the shaded area in FIG. 3).

X-Ray Line Sensor 14

Figure 4:
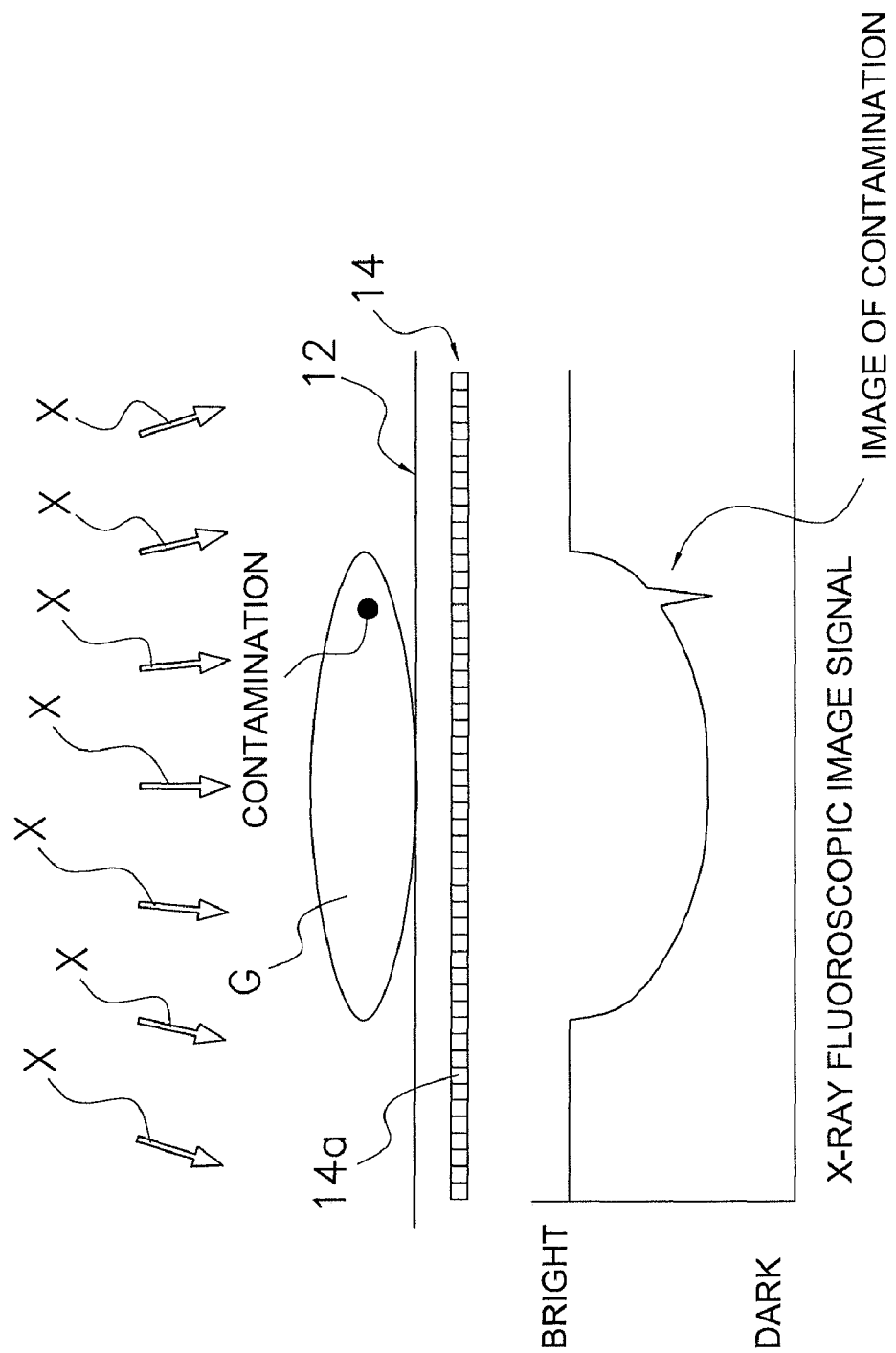
FIG. 4 is a schematic view showing the principle of inspection of contamination performed by the x-ray inspection apparatus in FIG. 1.

The x-ray line sensor 14 is disposed below the conveyor 12 (the opening 12c), and detects x-rays transmitted through the product G and the conveyor belt 12a. As shown in FIG. 3 and FIG. 4, this x-ray line sensor 14 comprises a plurality of pixels 14a arranged horizontally in a straight line in a direction perpendicular to the transport direction of the conveyor 12.

Note that FIG. 4 depicts a state in which x-rays are irradiated in the x-ray inspection apparatus 10 and a graph that indicates the amount of x-rays detected at that time at each pixel 14a constituting the x-ray line sensor 14.

Monitor 26

The monitor 26 is a full-dot liquid crystal display. In addition, the monitor 26 is equipped with a touch panel function and displays a screen that requests parameter input and the like regarding initial settings and determination after mass estimation.

In addition, the monitor 26 displays an x-ray transmission image of the product G, which is created based on the result of detection by the x-ray line sensor 14 and subsequently has undergone image processing. Accordingly, it is possible to have the user visually recognize a state inside the product G, for example, a state in which powder is concentrated in one portion and the like.

Control Computer 20

The control computer 20 executes, in a CPU 21, an image processing routine, an inspection determination processing routine, and the like, which are included in a control program. In addition, the control computer 20 saves and accumulates, in a storage unit such as a CF (CompactFlash®) 25, x-ray images and inspection results of defective products, correction data of x-ray images, and the like.

As a specific structure, as shown in FIG. 5, the control computer 20 comprises the CPU 21, and is also equipped with a ROM 22, a RAM 23, and the CF 25 as main storage units, which are controlled by the CPU 21.

The CF 25 stores various programs to control each unit, information regarding x-ray transmission images which serve as the basis of mass estimation, and the like.

Further, the control computer 20 is equipped with a display control circuit that controls the display of data on the monitor 26, a key input circuit that fetches key input data from the touch panel of the monitor 26, an I/O port for controlling data printing by a printer (not shown), and a USB 24 as an external connection terminal.

The CPU 21, the ROM 22, the RAM 23, the CF 25, and the like are connected each other through a bus line, such as an address bus or a data bus.

Further, the control computer 20 is connected to the conveyor motor 12f, a rotary encoder 12g, the x-ray irradiator 13, the x-ray line sensor 14, and a photoelectric sensor 15.

The control computer 20 receives the conveyance speed of the conveyor 12 detected by the rotary encoder 12g attached to the conveyor motor 12f.

In addition, the control computer 20 receives signals from the photoelectric sensor 15 as a synchronization sensor, which is configured from a light projecting device and its corresponding light receiving device disposed so as to sandwich the conveyor unit, and detects the timing at which the product G to be inspected reaches the position of the X-ray line sensor 14.

Function Block Created by the Control Computer 20

Figure 6:
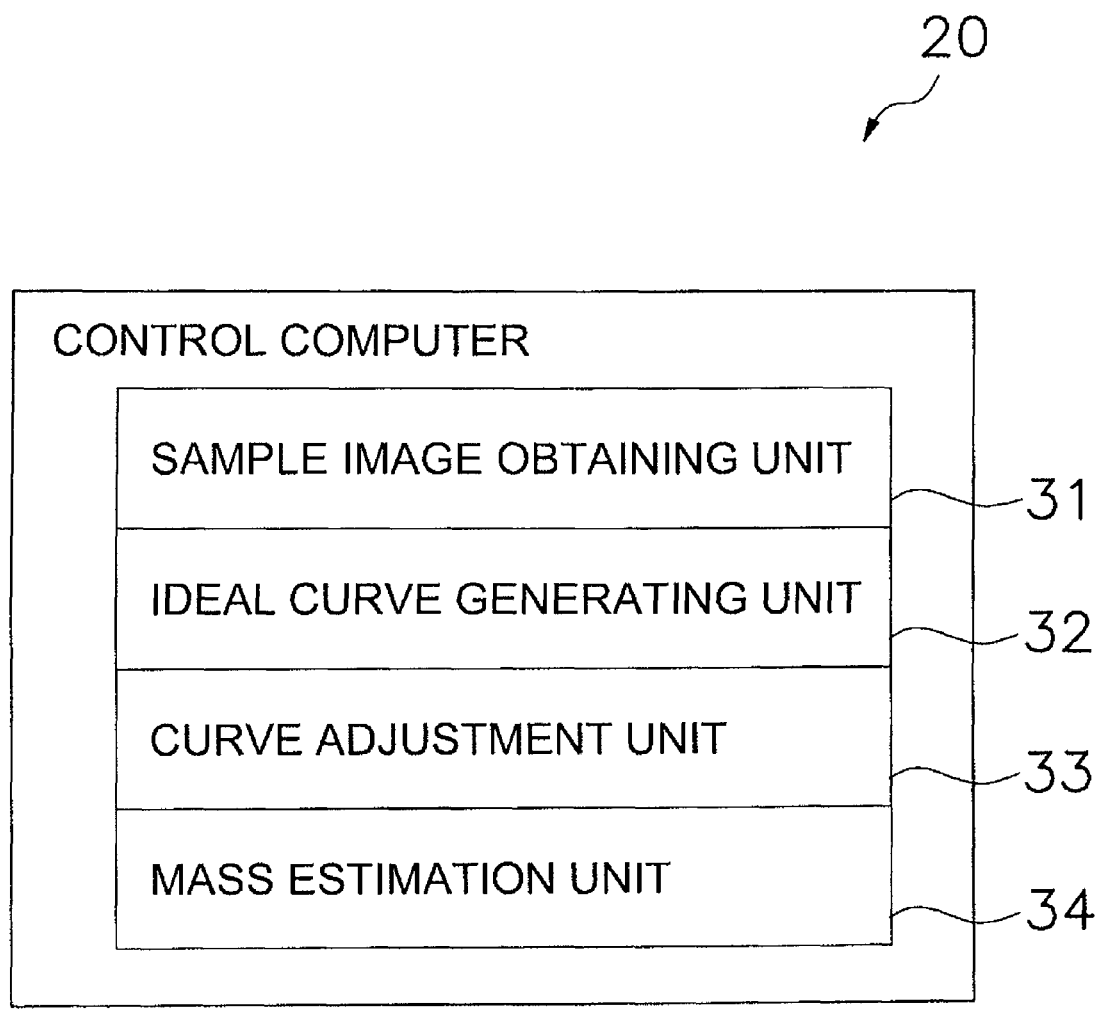
FIG. 6 is a function block diagram generated as a CPU of the control computer in FIG. 5 loads an x-ray inspection program.

In this embodiment, the CPU 21 of the control computer 20 loads an x-ray inspection program stored in the CF 25, and creates a function block as shown in FIG. 6.

Specifically, as shown in FIG. 6, a sample image obtaining unit 31, a table forming unit (ideal curve generating unit) 32, a table adjustment unit (curve adjustment unit) 33, and a mass estimation unit 34 are created as a function block in the control computer 20.

The sample image obtaining unit 31 obtains x-ray transmission images of 10 packaged powder soup products G each of whose mass is known in advance (hereinafter, the mass of each of the 10 packaged powder soup products G is referred to as the "actual mass").

For a brightness "a" per unit area (1 pixel) obtained by the sample image obtaining unit 31, the table forming unit 32 generates a table (ideal curve) m(a) based on the following formula (3) for calculating an estimated mass m of the area.

$$m = ct = -c/\mu \times \ln(I/I_0) = -\alpha \ln(I/I_0) \qquad (3)$$

(where, m: estimated mass, c: coefficient for converting the thickness of material to the mass, t: thickness of the material, $I_0$: brightness when there is no material, I: brightness when x-rays are transmitted through material, $\mu$: line absorption coefficient)

The table adjustment unit 33 compares the actual mass of each of 10 products G input via the monitor 26 to the total estimated mass of each product G obtained by adding up the estimated mass at each gradation level determined by the above table (ideal curve), and adjusts the table such that each total estimated mass approximates the actual mass.

The mass estimation unit 34 obtains the estimated mass per unit area according to the brightness per unit area (1 pixel) based on the table (ideal curve) adjusted by the table adjustment unit 33, and calculates the estimated mass of each product G by adding up these masses.

Note that a method for estimating the mass by each function block is described later in detail.

Control Flow for Mass Estimation by the Control Computer 20

Figure 7:
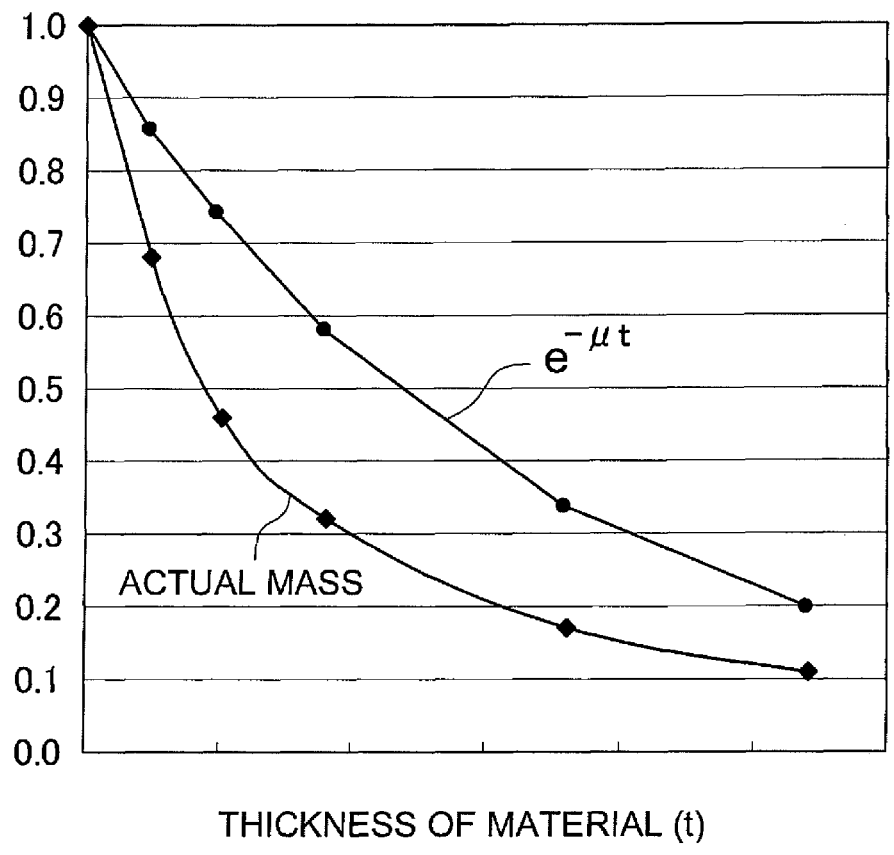
FIG. 7 is a graph that indicates a relationship between the brightness per unit area included in an x-ray transmission image and the thickness of material in the area.

In general, in the relationship between the thickness of material and the brightness of the corresponding portion (brightness when there is no material is defined as the normalized brightness of 1.0) in the x-ray transmission image obtained, it is known that errors are generated as shown in FIG. 7 between a graph ($I/I_0 = e^{-\mu t}$) represented by an exponential function as in the above described formula (I) and a graph indicating the actual masses. In particular, in the graph that indicates the actual mass, the brightness is drastically reduced in an area where the thickness "t" is relatively small. This occurs because an x-ray whose energy is relatively small is preferentially absorbed and the x-ray becomes harder as the x-ray passes through a material. Further, as described above, the brightness of the x-ray transmission image includes, in addition to factors such as x-ray energy distribution and the thickness of material, uncertain factors such as use of a specific filter, energy characteristics of the x-ray inspection apparatus, factors relating to image preprocessing such as gamma correction, and the like.

Figure 8:
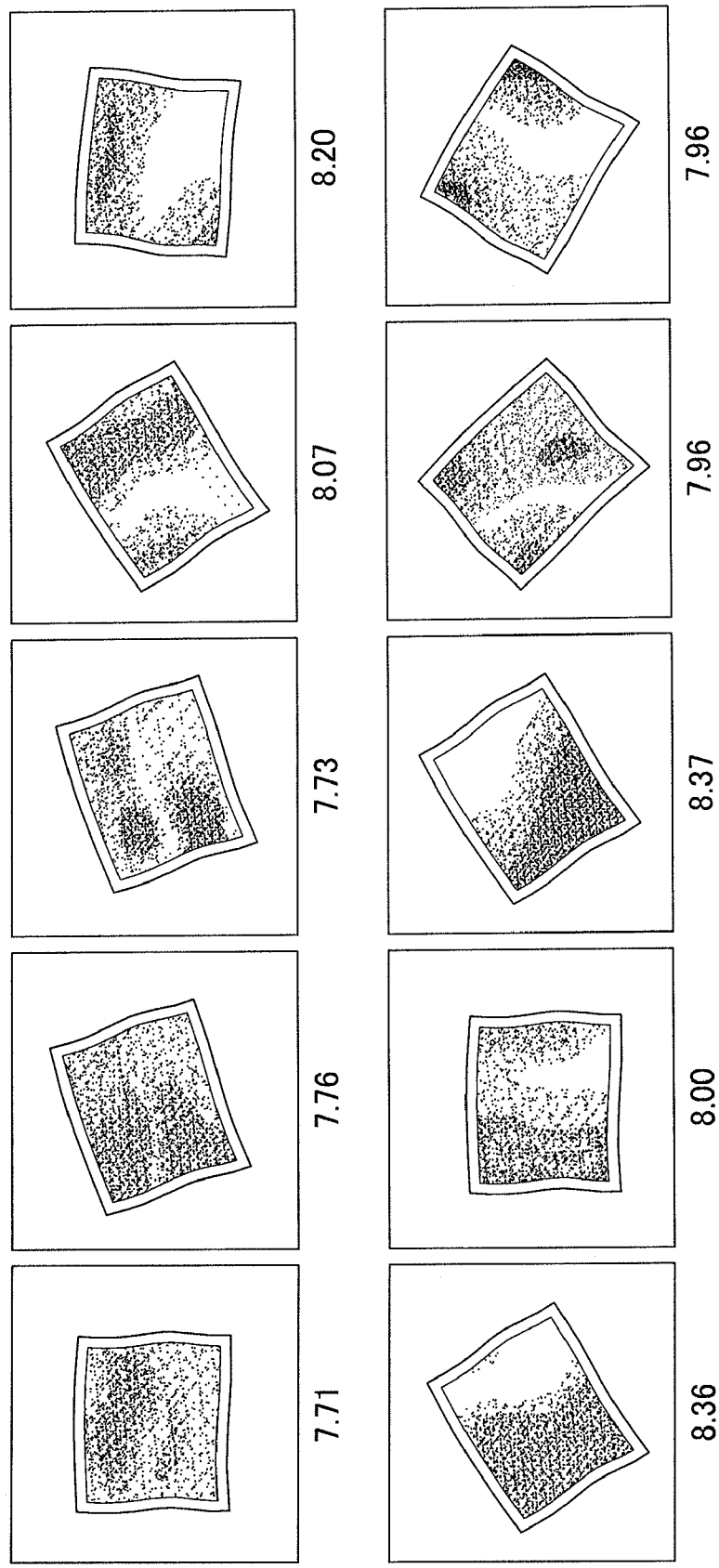
FIG. 8 shows 10 x-ray transmission images of products, which are obtained by the x-ray inspection apparatus in FIG. 1.

Here, FIG. 8 shows 10 x-ray transmission images of materials whose masses are estimated by using the products G having an actual mass of 8.0 grams. When compared to other x-ray transmission images, the x-ray transmission images at the left end and at the center in the lower column in each of which the powder is concentrated in one portion in the bag have larger estimated masses than the actual mass of 8.0 grams.

Figure 9:
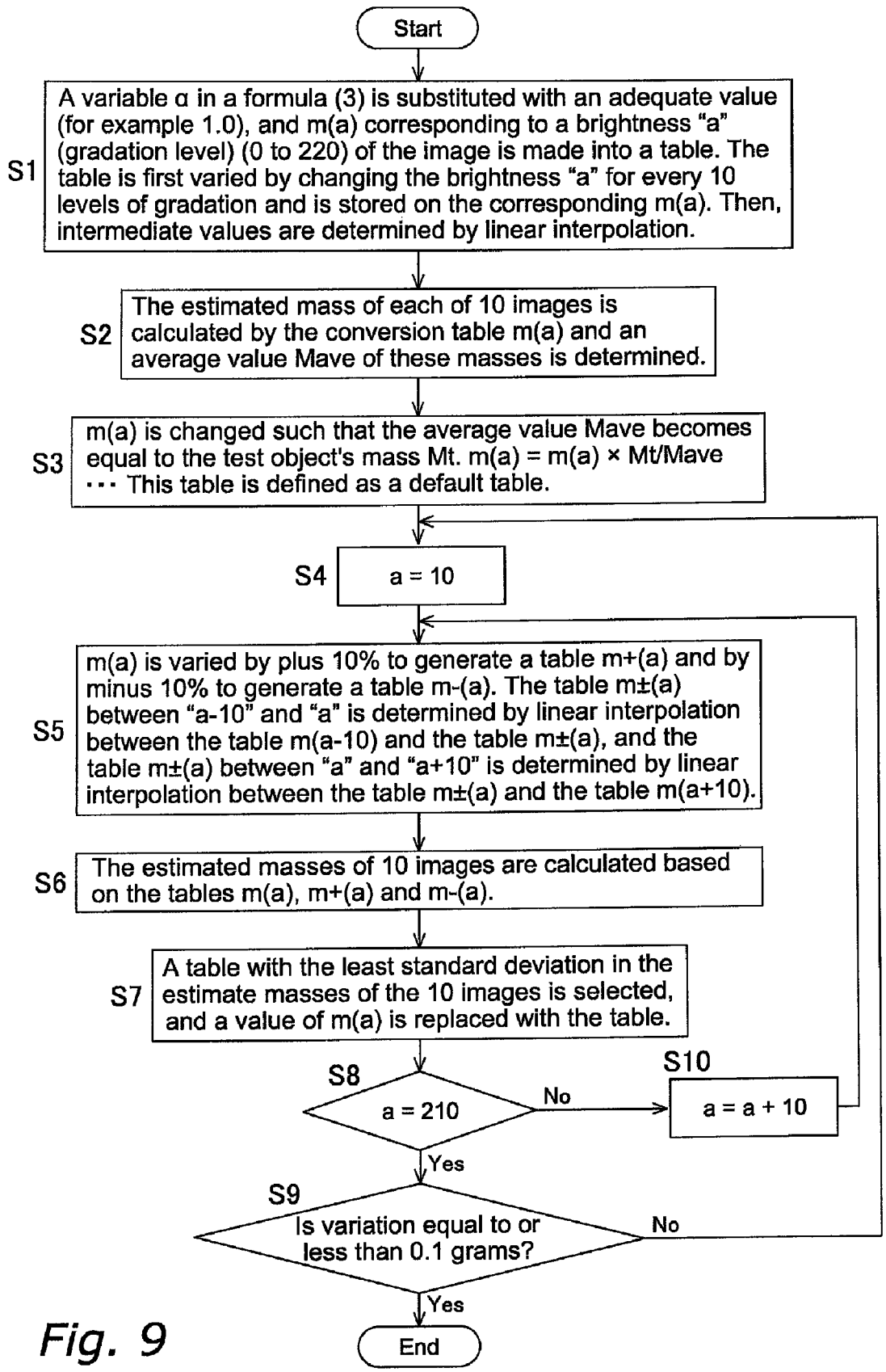
FIG. 9 is a flowchart showing a flow of a mass estimation method based on the x-ray inspection program by the x-ray inspection apparatus in FIG. 1.

With the x-ray inspection apparatus 10 in this embodiment, in view of the above described problem, estimation of the mass is performed according to the flowchart shown in FIG. 9, in order to estimate the mass with high accuracy by eliminating an uneven concentration of the powder in the bag of the product G and the influence of various uncertain factors.

In other words, in step S1, for example, a in the above described formula (3) is substituted with a value of 1.0, and the estimated mass m(a) corresponding to the image brightness (gradation level) "a" (0 to 220) is made into a table. The table generated based on the formula (3) is first varied by changing the brightness "a" for every ten levels of gradation and is stored on a table corresponding to m(a). Then, intermediate values are determined by linear interpolation.

Figure 10A:
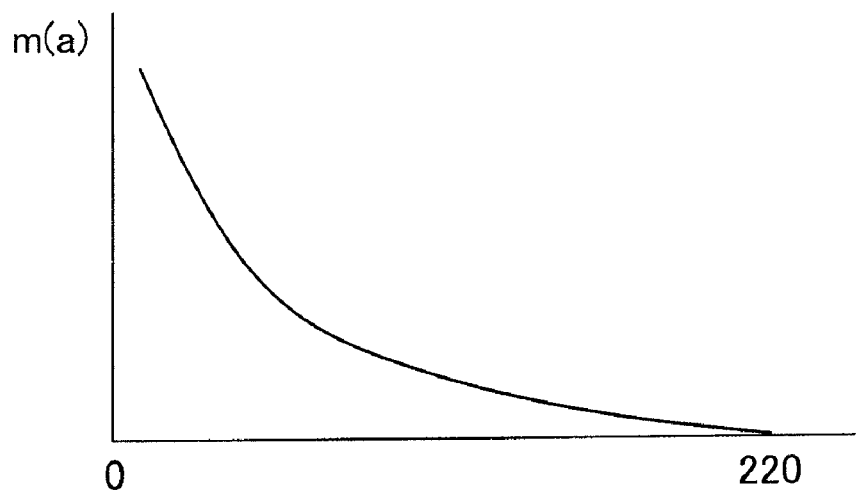
FIG. 10A is a graph showing a table m(a) before a coefficient α is optimized.

Accordingly, the table forming unit 32 of the control computer 20 generates a table (ideal curve) as shown in FIG. 10A, which indicates a relationship between the brightness and the estimated mass m(a). Note that, in view of that it takes too much time to obtain the estimated mass of the unit area at each brightness level according to the formula (3), here, the estimated mass is obtained for every ten levels of gradation and the intermediate values are determined by linear interpolation.

In step S2, as shown in FIG. 8, the sample image obtaining unit 31 irradiates x-rays to 10 sample inspected products G each of whose mass is known to be 8.0 grams in advance and thereby obtains 10 x-ray transmission images. Then, the estimated masses of the 10 x-ray transmission images obtained are calculated by the conversion table m(a), and an average value Mave of these masses is determined. Note that, in order to obtain a broader range of brightness data, it is preferable that 10 sample images include an image of a product in which the powder is concentrated in one portion in the bag, an image of a product in which the powder is evenly dispersed, and the like.

Figure 10B:
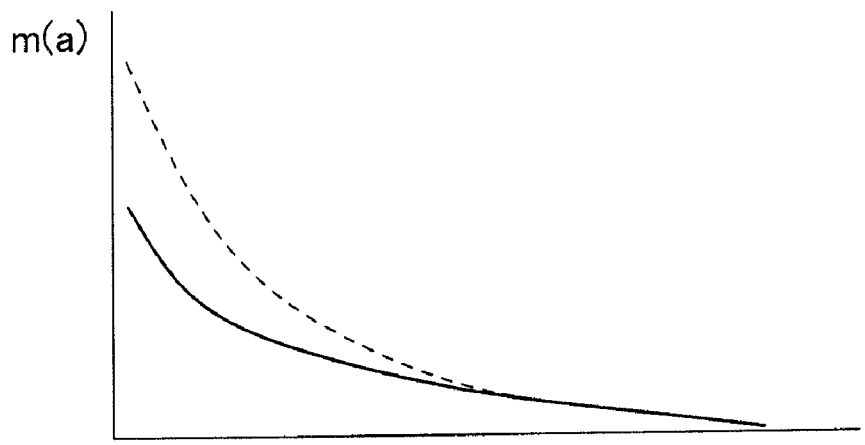
FIG. 10B is a graph showing a table m(a) after the coefficient α is optimized.

In step S3, m(a) is changed according to the following relational expression (5) such that the average value Mave determined in step S2 becomes equal to the inspected object's mass Mt (e.g., 8.0 grams), and a table after the change as shown by a solid line in FIG. 10B is defined as a default table (ideal curve). Note that in FIG. 10B, the dotted line indicates a table before the change, and the solid line indicates a default table (ideal curve) after the change.

$$m(a) = m(a) \times Mt/Mave \qquad (5)$$

In step S4, a value 10 is substituted for the brightness "a" in the table m(a) prepared in step S3 in order to determine the estimated mass m(a) (reference estimated mass). Here, the brightness "a" is substituted by a number starting with a value 10, and then 20, 30, . . . . This is because the estimated mass would become infinite if the brightness "a" is substituted by a value 0. Accordingly, it is possible to start substituting a value 1 for the brightness "a" followed by values 11, 21, 31, . . . to determine the estimated mass.

In step S5, in order to examine changes caused by gradually shifting the table m(a) up and down, the table m(a) is varied by plus 2% and minus 2% to generate a new table m+(a) (upper estimated mass) and a new table m−(a) (lower estimated mass), respectively. At this time, the table m+(a) between "a−10" and "a" is determined by linear interpolation between the table m(a−10) and the table m+(a), and the table m+(a) between "a+10" and "a" is determined by linear interpolation between the table m+(a) and the table m(a+10). Likewise, the table m−(a) between "a−10" and "a" is determined by linear interpolation between the table m(a−10) and the table m−(a), and the table m−(a) between "a+10" and "a" is determined by linear interpolation between the table m−(a) and the table m(a+10). Therefore, the table m+(a) and the table m−(a) are generated.

In step S6, the estimated masses of 10 x-ray transmission images are calculated based on the two new tables generated in step S5, i.e., the table m+(a) and the table m−(a), and the original table m(a).

In step S7, a table with the least standard deviation (least variation) based on the estimated masses corresponding to each of the ten x-ray transmission images, which are calculated by using the three tables m(a), m+(a), and m−(a) in step S6, is selected, and the table m(a) is replaced with this table.

For example, when the table m+(a) has lower standard deviation than the table m(a) in a certain brightness (gradation level) "a", the table m(a) is replaced with the table m+(a) for a portion corresponding to the brightness "a." On the other hand, when the table m(a) has lower standard deviation than the table m+(a), the table m(a) will not be replaced but maintained as is for a portion corresponding to the brightness "a".

Figure 11A:
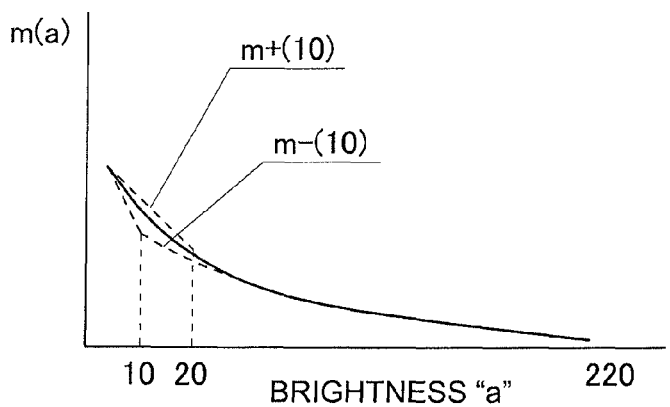
FIGS. 11(a) to (c) are graphs to represent a process in which a conversion table m(a) is optimized.
Figure 11B:
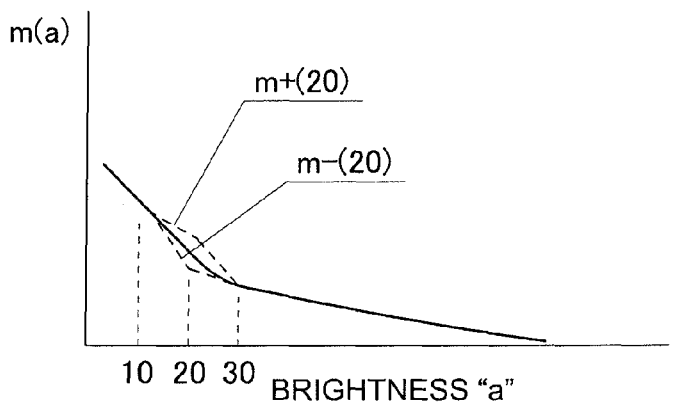

Specifically, as shown in FIG. 11A, in a portion where the brightness (a) is equal to 10, the standard deviation is compared among the table m(10) shown by a solid line, the table m+(10) shown by a dotted line above, and the table m-(10) shown by a dotted line below, and the table m+(10) with the least standard deviation is selected. Consequently, as shown in FIG. 11B, in a portion where the brightness (a) is equal to 10, the table m (10) is replaced with the table m+(10).

In step S8, whether or not the brightness "a" is 210 is determined, and when the answer is "no," the process proceeds to step S10, and the replacement process of the table m(a) in the above described step S7 is repeated by increasing the brightness "a" by 10 until the brightness "a" is 210.

Figure 11C:
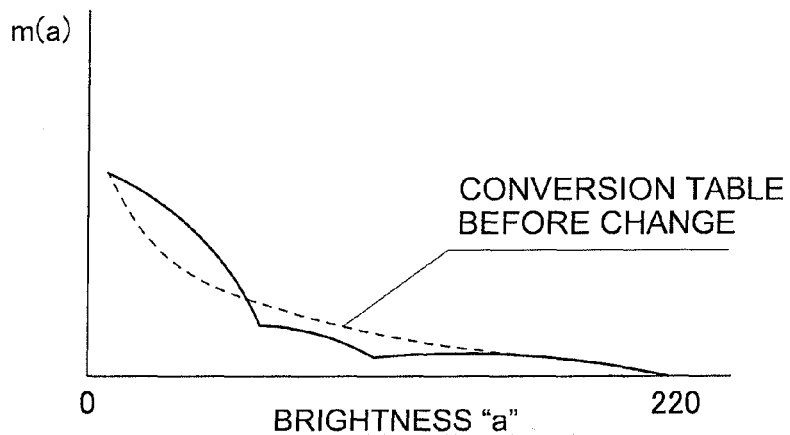

In other words, replacement of the table is repeated in the same way for cases where the brightness "a" is equal to 20, 30, 40, . . . , in order to generate the table shown by a solid line in FIG. 11C.

Note that the process in step S7 corresponds to the adjustment process of the table, i.e., the ideal curve performed by the table adjustment unit 33.

In step S9, the masses of the ten x-ray transmission images are determined in accordance with the post-adjusted table m(a) obtained by the replacement process, and whether or not the value of variation in the mass is equal to or less than 0.1 grams. Here, when the value is equal to or greater than 0.1 grams, the process returns to step S4 and the above described process is repeated until the value of variation become equal to or less than 0.1 grams.

Through the above described process, the x-ray inspection apparatus 10 of the present invention generates the conversion table m(a) (see FIG. 11C) for estimating the mass of the product G from the x-ray transmission image of the product G. Accordingly, by estimating the mass of the product G to be inspected by using the optimized, post-adjusted conversion table m(a) as shown in FIG. 11C, it is possible to achieve estimation of the mass with high accuracy, compared to the conventional mass estimation method that depends on the formula.

Here, FIG. 13 shows the results of inspection of the product G having an actual mass of 10.0 grams, which was performed by using the conversion tables before and after optimization.

Figure 12A:
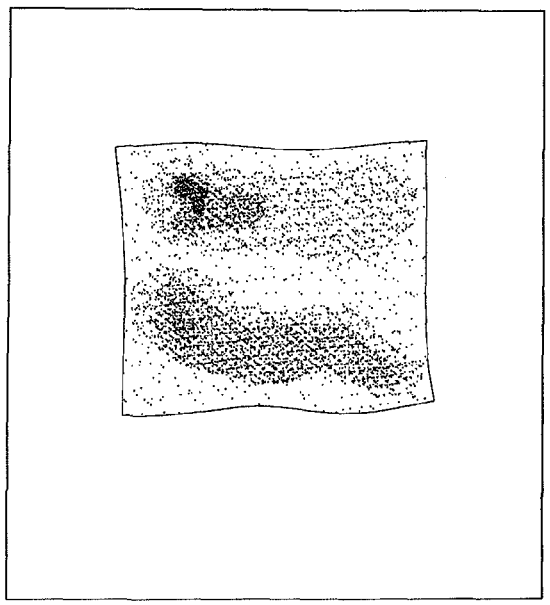
FIG. 12A shows an example of an x-ray transmission image of a product G in which powder is dispersed substantially evenly in a bag.
Figure 12B:
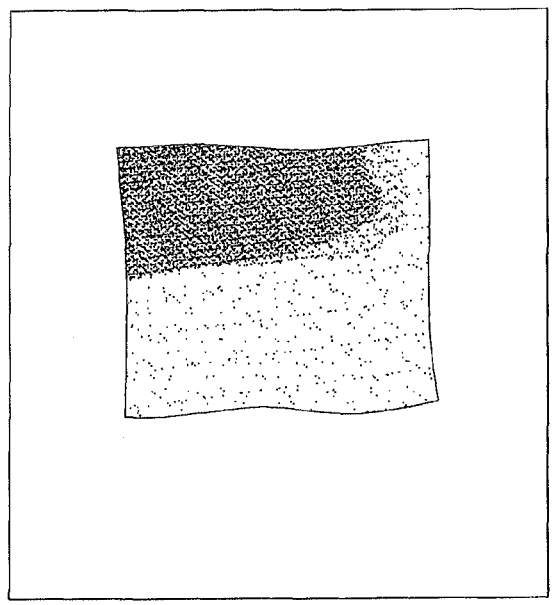
FIG. 12B shows another example in which powder is concentrated in one portion in a bag.

According to the results obtained by using the unoptimized conversion table m(a), as shown in FIG. 12A and FIG. 12B, an error in the estimated masses between the one in which the powder is evenly distributed in the bag (10.34 grams) and the one in which the powder is concentrated in one portion (9.79 grams) is 0.55 grams; whereas according to the results obtained by using the conversion table m(a) that is optimized according to the above described flowchart shown in FIG. 9, an error in the estimated mass between the one in which the powder is evenly distributed in the bag (10.03 grams) and the one in which the powder is concentrated in one portion (9.95 grams) is as small as 0.08 grams. Further, an error with respect to an actual mass of 10.0 gram is significantly smaller in the estimated masses determined based on the optimized conversion table. Specifically, the error is reduced from 0.34 grams to 0.03 grams in the bag in which the powder is evenly distributed and from 0.21 grams to 0.05 grams in the bag in which the powder is concentrated in one portion.

In this way, the results shown in FIG. 13 shows that it is possible to determine the estimated mass of the product G with higher accuracy compared to the conventional method, by calculating the estimated mass based on the conversion table m(a) optimized according to the flowchart shown in FIG. 9.

Characteristic of the X-Ray Inspection Apparatus 10

(1) With the x-ray inspection apparatus 10 in this embodiment, as shown in FIG. 5, the function block as shown in FIG. 6 is generated as the CPU 21 installed in the control computer 20 loads the x-ray inspection program stored in the CF 25. This function block includes the sample image obtaining unit 31, the table forming unit 32, the table adjustment unit 33, and the mass estimation unit 34. The sample image obtaining unit 31 obtains 10 x-ray transmission images of the products G each of whose mass is known in advance. The table forming unit 32 generates the table (ideal curve) m(a) based on the above described formula (3) which indicates a relationship between the brightness per unit area included in the x-ray transmission images and the estimated mass of the area. The table adjustment unit 33 refers to the actual mass of material whose x-ray transmission image is input via the monitor 26 and adjusts the table m(a) for every ten levels of gradation such that the estimated mass approximates the actual mass. The mass estimation unit 34 determines the estimated mass per unit area based on the post-adjusted table m(a) and adds up these values in order to determine the total estimated mass of the product G.

Accordingly, by determining the estimated mass by using the table m(a) adjusted with reference to the actual mass, it is possible to obtain a highly accurate estimated mass that is more approximate to the actual mass, compared to the conventional method in which the estimated mass is determined by using the table m(a) generated based on the formula (3) as is.

(2) With the x-ray inspection apparatus 10 in this embodiment, the table m(a) generated by the table forming unit 32 is varied by plus minus 2% in order to generate a new table m+(a) and a new table m−(a), and as shown in FIG. 11A to FIG. 11C, these tables m(a), m+(a), m−(a) are compared for every predetermined gradation level, and the table m(a) is adjusted through repeated replacement of m(a) with the one having the least standard deviation.

Accordingly, since the table m(a) generated based on the formula (3) can be optimized so as to enable estimation of the mass that is more approximate to the actual mass, it is possible to obtain the estimated mass with higher accuracy than it is possible with the conventional method.

(3) With the x-ray inspection apparatus 10 in this embodiment, as shown in step S8 in FIG. 9, the optimization process (replacement) of the above mentioned table m(a) is repeated by increasing the brightness "a" for every ten levels of gradation in the range from the graduation level 10 to the gradation level 210.

Accordingly, by specifying a condition that the optimization process of the table m(a) is terminated when a predetermined gradation level is obtained as a termination condition, it is possible to obtain the table m(a) optimized for each gradation level (brightness). As a result, it is possible to estimate the mass with higher accuracy.

(4) With the x-ray inspection apparatus 10 in this embodiment, as shown in step S9 in FIG. 9, the optimization process (replacement) of the above described table m(a) is repeated until the value of variation in the estimated masses of the ten x-ray transmission images becomes equal to or less than 0.1 grams.

Accordingly, by repeating the optimization process of the table m(a) which serves as the basis of determination of the estimated mass until the variation becomes equal to or less then a predetermined value, it is possible to further thoroughly optimize the table m(a) and determine the estimated mass with high accuracy. In addition, as shown in step S8 and step S9 in FIG. 9, as the termination conditions of the optimization process of the table m(a), the first condition in which the process is terminated when a predetermined gradation level is obtained and the second condition in which the process is terminated when variation becomes equal to or less than a predetermined value are combined, and the table m(a) can be adjusted more thoroughly and thus it is possible to determine the estimated mass with higher accuracy.

(5) With the x-ray inspection apparatus 10 in this embodiment, as shown in step S1 in FIG. 9, the brightness "a" is changed for every ten levels of gradation, the estimated mass is calculated based on the formula (3), and linear interpolation is used to determine the intermediate values in order to generate the table m(a).

Accordingly, it is possible to significantly reduce the time to generate the table m(a) and efficiently determine the estimated mass, compared to a case where the table m(a) is generated for the entire gradation levels in the table m(a) by using the formula (3).

(6) With the x-ray inspection apparatus 10 in this embodiment, the table m(a) which indicates a relationship between the brightness "a" per unit area included in the x-ray transmission images and the estimated mass of the area is used as a tool for determining the estimated mass.

Accordingly, it is possible to significantly reduce the time to calculate the estimated mass, compared to a method in which the estimated mass is determined based on the formula.

(7) With the x-ray inspection apparatus 10 in this embodiment, as a unit area included in the x-ray transmission image, the brightness per 1 pixel and the corresponding estimated mass are determined.

Accordingly, by determining the estimated mass with one pixel as a unit, which is the maximum unit in the x-ray transmission image, it is possible to obtain the estimated mass with higher accuracy.

ALTERNATIVE EMBODIMENTS

While preferred embodiments have been described in connection with the present invention, the scope of the present invention is not limited to the above embodiments, and various changes and modifications may be made without departing from the scope of the present invention.

(A) The above embodiment is described using an example in which the table m(a), which indicates a relationship between the brightness "a" per unit area included in an x-ray transmission image and the estimated mass of the area, is generated in order to determine the estimated mass of the product G. However, the present invention is not limited thereto.

For example, the table m(a) does not have to be necessarily generated, and a formula may be used when the relationship can be expressed by such a formula. However, when the estimated mass is determined by using the table m(a) as is the case in the above described embodiment, the processing time to determine the estimated mass is significantly reduced compared to the case where a formula is used. Therefore, it is more preferable to use a table as is the case in the above described embodiment.

(B) The above embodiment is described using an example in which, as shown in FIG. 9, the loop of step S5 to step S8 in the optimization process of the table m(a) is repeated by increasing the brightness "a" for every ten levels of gradation until the maximum gradation level 220 is obtained. However, the present invention is not limited thereto.

As the termination condition of the optimization process, the optimization process does not have to be terminated when the gradation level 220 is obtained. For example, the optimization process may be terminated when another gradation level is obtained. Or, the optimization process may be controlled so as to be terminated after the optimization process is repeated for a predetermined for number of times or after a predetermined period of time has elapsed. Or, a plurality of these termination conditions may be combined.

(C) The above embodiment is described using an example in which the loop of step S4 to step S10 in the optimization process of the table m(a) is repeated until the value of variation become equal to or less than 0.1 grams. However, the present invention is not limited thereto.

The termination condition of the optimization process does not have to be the case where the value of variation becomes equal to or less than 0.1 grams. For example, the optimization process may be terminated when the value of variation becomes below a different value other than 0.1 grams. Or, the optimization process may be controlled so as to be terminated after the optimization process is repeated for a predetermined number of times or after a predetermined period of time has elapsed. Or, a plurality of these termination conditions may be combined.

(D) The above embodiment is described using an example in which the 10 x-ray transmission images of 10 products G each of whose mass is known in advance are obtained as the sample x-ray transmission images. However, the present invention is not limited thereto.

The number of sample images is not limited to 10. For example, the number may be 5 or less, or 20 or more.

(E) The above embodiment is described using an example in which, among the estimated masses m(a), m+(a), and m−(a), the one with the least standard deviation is selected and the replacement process of m(a) is performed. However, the present invention is not limited thereto.

For example, selection does not have to be necessarily based on the standard deviation. Other variation elements such as dispersion and the like may be observed as the basis of selection.

(F) The above embodiment is described using an example in which the present invention is applied to the x-ray inspection apparatus 10. However, the present invention is not limited thereto.

For example, the present invention is applicable to the x-ray inspection program stored in the memory unit of the x-ray inspection apparatus. In such a case, the CPU loads this x-ray inspection program so as to cause the computer to execute the x-ray inspection method which is performed according to the flowchart shown in FIG. 9.

(G) The above embodiment is described using an example in which, in step S5, in order to examine changes caused by gradually shifting the table m(a) up and down, the table m(a) is varied by plus minus 2% in order to generate a new table m+(a) and a new table m−(a). At this time, the table m+(a) between "a−10" and "a" is determined by linear interpolation between m(a−10) and m+(a), and the table m+(a) between "a+10" and "a" is determined by linear interpolation between m+(a) and m(a+10), in order to generate the table m+(a). Likewise, the table m−(a) between "a−10" and "a" is determined by linear interpolation between m(a−10) and m−(a), and the table m−(a) between "a+10" and "a" is determined by linear interpolation between m−(a) and m(a+10), in order to generate and the table m−(a). However, the present invention is not limited thereto.

Figure 14:
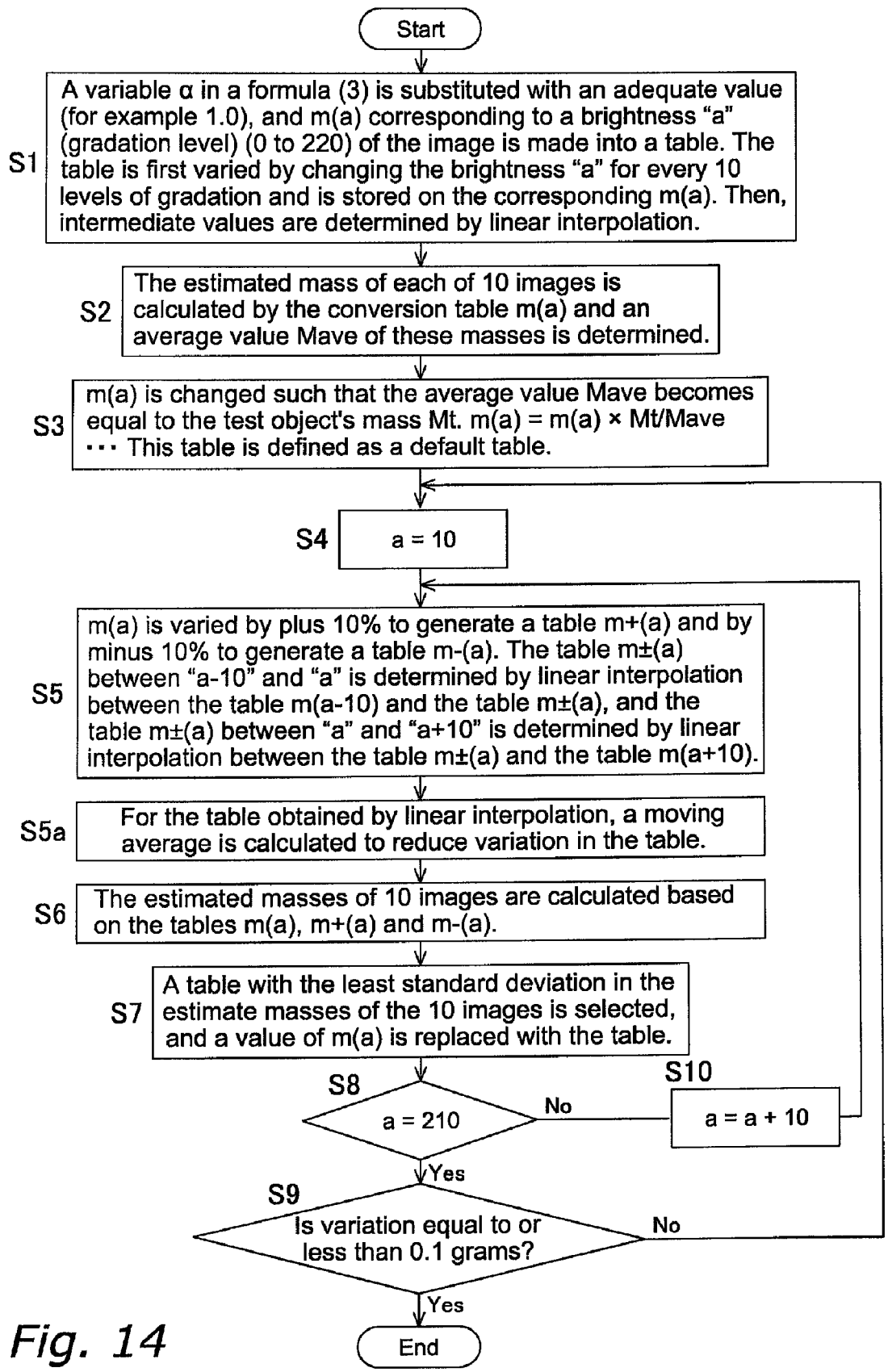
FIG. 14 is a flowchart showing a flow of an x-ray inspection method executed by an x-ray inspection apparatus according to another embodiment of the present invention.

For example, as shown in FIG. 14, step S5a may be inserted after step S5 in order to adjust the obtained table by linear interpolation.

Specifically, in step S5a, for the table obtained by linear interpolation, a moving average is calculated based on the following formula (6) and the table is adjusted such that table produces a smooth curve when the table is converted to a graph, thereby reducing the variation in the table (variation in the estimated mass).

$$F(x) = \left(\sum_{x=-n}^{n} f(x+X)\right) \Big/ (2n+1) \qquad (6)$$

In this way, it is possible to prevent that the estimated mass is changed in a discontinuous manner by a small change in the brightness in each pixel, compared to the case where the table generated by linear interpolation is used. Therefore, it is possible to highly accurately calculate the estimated mass.

(H) The above embodiment is described using an example in which, in step S1, the brightness "a" is changed for every ten levels of gradation and stored on a table corresponding to m(a), and intermediate values are determined by linear interpolation. Then, the table forming unit 32 of the control computer 20 generates the table (ideal curve) as shown in FIG. 10A, which indicates a relationship between the brightness and the estimated mass m(a). However, the present invention is not limited thereto.

Figure 15:
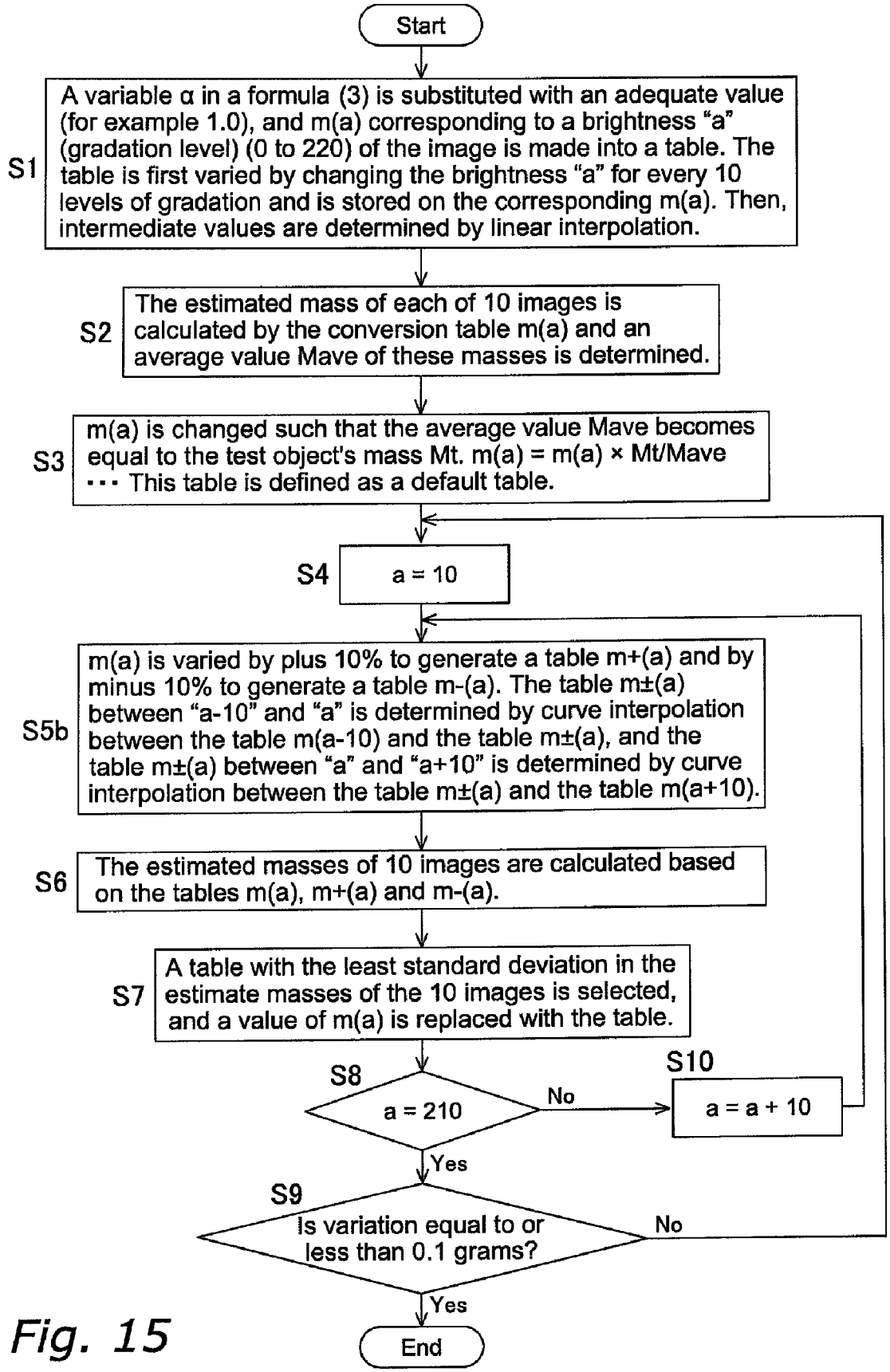
FIG. 15 is a flowchart showing a flow of an x-ray inspection method executed by an x-ray inspection apparatus according to yet another embodiment of the present invention.

For example, as shown in FIG. 15, step S5b may be inserted instead of step S5, in order to adjust the table obtained by curve interpolation.

Specifically, in step S5b, m(a) (reference estimated mass) is varied by plus 10% to generate a new table m+(a) (upper estimated mass) and by minus 10% to generate a new table m−(a) (lower estimated mass). The table m+(a) between "a−10" and "a" is determined by curve interpolation between the table m(a−10) and the table m+(a), and the table between "a+10" and "a" is determined by curve interpolation between the table m+(a) and the table m(a+10). Likewise, the table m−(a) between "a−10" and "a" is determined by curve interpolation between the table m(a−10) and the table m−(a), and the table m−(a) between "a+10" and "a" is determined by curve interpolation between the table m−(a) and the table m(a+10).

Figure 16:
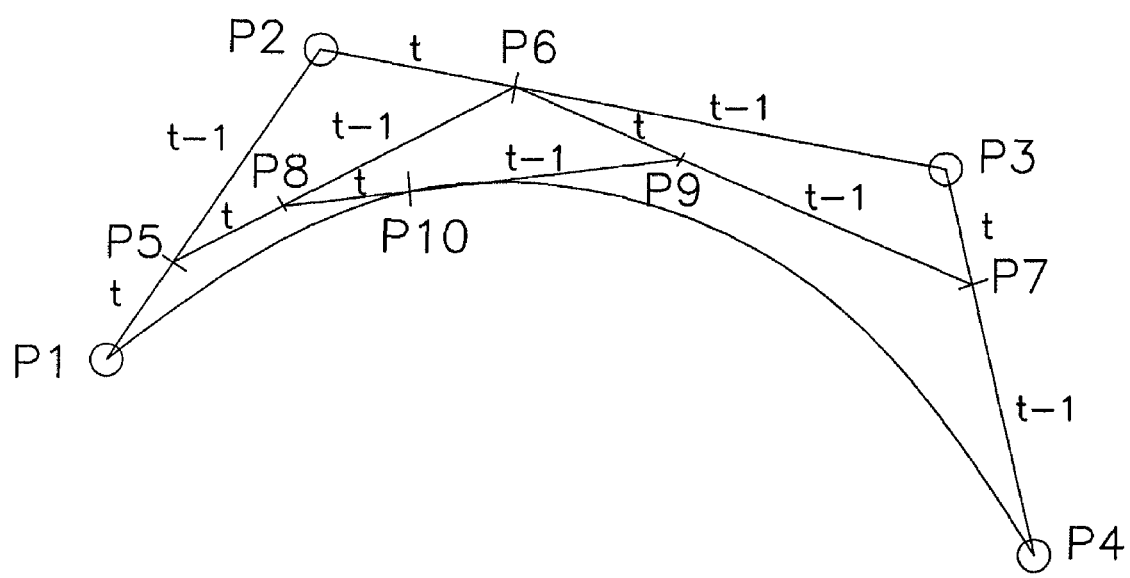
FIG. 16 is an illustration to show a concept of curve interpolation implemented in the flowchart in FIG. 15.

As a curve interpolation method, an interpolation method using a so-called Bezier curve, which is a method to approximate with N function, may be used as shown in FIG. 16. Accordingly, when an interpolation method using a so-called Bezier curve with an N number of control points is adopted, it is possible to interpolate a curve by an N-variable linear function. For example, when a curve connecting four control points is generated, it is possible to obtain a curve represented by a cubic function. In other words, when four control points P1 to P4 shown in FIG. 16 are provided, first, a point P5 is specified which divides the control points P1 to P2 in the ratio t:1−t. Likewise, a point P6 and a point P7 which respectively divide the points P2 to P3 and the points P3 to P4 in the same ratio, are specified. Next, a point P8 and a point P9, which respectively divide the points P5 to P6 and the points P6 to P7 in the same ratio, are specified. Then, a point P10 that divides the points P8 to P9 in the same ratio is determined. This operation is executed for $0 \leq t \leq 1$ in a continuous manner, and a Bezier curve is drawn along the locus of the point P10, thereby interpolating the curve.

As a result, it is possible to prevent that the estimated mass is changed in a discontinuous manner by a small change in the brightness in each pixel, compared to the case where the table generated by linear interpolation is used. Therefore, it is possible to calculate the estimated mass with higher accuracy.

Note that a curve interpolation method is not limited to the methods described in the above alternative embodiments (G) and (H). For example, it is possible to interpolate a curve by using a spline curve and the like.

The x-ray inspection apparatus of the present invention produces an effect of obtaining the estimated mass with higher accuracy compared to the conventional apparatus, and therefore this x-ray inspection apparatus is broadly applicable to x-ray mass estimation apparatuses configured to estimate the mass from the brightness of an area included in x-ray transmission image.

The invention claimed is:

1. An x-ray inspection apparatus comprising:
   an irradiation unit configured and arranged to irradiate x-rays to an inspected object;
   an x-ray detection unit configured and arranged to detect an amount of x-rays that are irradiated by the irradiation unit and transmitted through the inspected object;
   a sample image obtaining unit configured to obtain a plurality of sample x-ray transmission images of a plurality of sample inspected objects based on an amount of x-rays irradiated to each of the sample inspected objects detected by the x-ray detection unit;
   an input unit configured to receive inputs of actual masses of the sample inspected objects;
   an ideal curve generating unit configured to generate an ideal curve which indicates a mass per unit area with respect to a brightness per unit area included in the sample x-ray transmission images;
   a curve adjustment unit configured to adjust the ideal curve generated by the ideal curve generating unit for a plurality of gradation levels based on the actual masses input in the input unit; and
   a mass estimation unit configured to estimate a mass of the inspected object based on the amount of x-rays irradiated to the inspected object and detected by the x-ray detection unit according to the ideal curve adjusted by the curve adjustment unit.

2. The x-ray inspection apparatus according to claim 1, wherein
   the curve adjustment unit is further configured
      to determine a reference estimated mass that corresponds to the brightness of one of the graduation levels per unit area, an upper estimated mass that corresponds to a value that is larger than the reference estimated mass by a prescribed percentage, and a lower estimated mass that corresponds to a value that is smaller than the reference estimated mass by the prescribed percentage,
      to select one of the reference estimated mass, the upper estimated mass and the lower estimated mass that provides a least variation when the masses of the sample inspected objects are estimated by using the reference estimated mass, the upper estimated mass and the lower estimated mass for the one of the graduation levels, and
      to adjust the ideal curve by replacing a value of the mass per unit area corresponding to the brightness of the one of the graduation levels in the ideal curve with the one of the reference estimated mass, the upper estimated mass and the lower estimated mass that was selected.

3. The x-ray inspection apparatus according to claim 2, wherein
the curve adjustment unit is configured to repeat replacing the value of the mass per unit area for the brightness of each of the graduation levels until the brightness reaches a predetermined gradation level.

4. The x-ray inspection apparatus according to claim 2, wherein
the curve adjustment unit is configured to repeat replacing the value of the mass per unit area for the brightness of each of the graduation levels until a variation in estimated masses of the sample inspected objects estimated by using the ideal curve falls within a predetermined range.

5. The x-ray inspection apparatus according to claim 2, wherein
the curve adjustment unit is configured to repeat replacing the value of the mass per unit area for the brightness of each of the graduation levels for a predetermined number of times.

6. The x-ray inspection apparatus according to claim 2, wherein
the curve adjustment unit is configured to repeat replacing the value of the mass per unit area for the brightness of each of the graduation levels until a predetermined period of time elapses.

7. The x-ray inspection apparatus according to claim 1, wherein
the ideal curve generating unit is configured to calculate the mass per unit area corresponding to the brightness for every ten levels of gradation, and to generate the ideal curve by linear interpolation of intermediate values.

8. The x-ray inspection apparatus according to claim 1, wherein
the ideal curve generating unit is configured to generate a table that indicates a relationship between the brightness with respect to an estimated mass for the brightness based on a predetermined formula that represents the mass per unit area with respect to the brightness per unit area included in an x-ray transmission image.

9. The x-ray inspection apparatus according to claim 1, wherein
the unit area corresponds to one pixel in an x-ray transmission image.

10. The x-ray inspection apparatus according to claim 1, wherein
the ideal curve generating unit is configured to calculate the mass per unit area corresponding to the brightness for every ten levels of gradation, and to generate the ideal curve by calculating a moving average of a function obtained by linear interpolation of intermediate values.

11. The x-ray inspection apparatus according to claim 1, wherein
the ideal curve generating unit is configured to calculate the masses per unit area corresponding to the brightness for every ten levels of gradation, and to generate the ideal curve by curve interpolation of intermediate values.

12. A non-transitory computer readable medium encoded with an x-ray inspection program which, when implemented on a computer, configures the computer to estimate a mass of an inspected object based on an amount of transmitted x-rays that are irradiated to the inspected object and further configures the computer to perform
a first step in which an amount of x-rays that are irradiated to a plurality of the sample inspected objects is detected, and x-ray transmission images of the sample inspected objects are obtained based on the amount of x-rays detected;
a second step in which inputs of actual masses of the sample inspected objects whose x-ray transmission images are obtained in the first step are received;
a third step in which an ideal curve derived based on a mass per unit are with respect a brightness per unit area included in the x-ray transmission images is generated;
a fourth step in which the ideal curve generated in the third step is adjusted for a plurality of gradation levels based on the actual masses input in the second step; and
a fifth step in which the mass of the inspected object is estimated based on the ideal curve adjusted in the fourth step.

* * * * *